(12) United States Patent
Bright

(10) Patent No.: US 7,448,380 B2
(45) Date of Patent: Nov. 11, 2008

(54) COMPRESSOR UNIT FOR NEBULIZER

(75) Inventor: Craig Jeremy Bright, Hilton Head Island, SC (US)

(73) Assignee: Medquip, Inc, Hilton Head, SC (US)

( * ) Notice: Subject to any disclaimer, the term of this patent is extended or adjusted under 35 U.S.C. 154(b) by 346 days.

(21) Appl. No.: 11/385,189

(22) Filed: Mar. 21, 2006

(65) Prior Publication Data
US 2007/0221220 A1    Sep. 27, 2007

(51) Int. Cl.
*A61M 11/00* (2006.01)
(52) U.S. Cl. ............... 128/203.16; 128/204.18
(58) Field of Classification Search ............ 128/200.14, 128/200.21, 200.11, 200.24, 203.28, 204.18, 128/203.12
See application file for complete search history.

(56) References Cited

U.S. PATENT DOCUMENTS

| | | | | |
|---|---|---|---|---|
| 4,257,415 A * | 3/1981 | Rubin | .................. | 128/200.21 |
| 4,949,715 A * | 8/1990 | Brugger | .................. | 128/204.21 |
| 5,357,945 A * | 10/1994 | Messina | ................ | 128/200.14 |
| H1557 H * | 7/1996 | Joubert et al. | ................ | 600/590 |
| 5,779,515 A * | 7/1998 | Chung | .......................... | 446/90 |
| 5,853,002 A * | 12/1998 | Kawasaki | .............. | 128/200.14 |
| 6,979,245 B1 * | 12/2005 | Goodwin | ..................... | 446/149 |
| 7,350,520 B1 * | 4/2008 | Richard-Bey | .......... | 128/200.21 |
| 2006/0100021 A1 * | 5/2006 | Yoshino et al. | ............... | 463/45 |

* cited by examiner

*Primary Examiner*—Steven O Douglas
(74) *Attorney, Agent, or Firm*—Thomas, Kayden, Horstemeyer & Risley

(57) ABSTRACT

The systems disclosed herein relate to medical nebulizer systems, and more specifically interactive nebulizer compressors. In one embodiment an interactive nebulizer compressor includes an air compressor configured to output a pressurized gas. The embodiment further includes an enclosure surrounding the air compressor and a tubing coupler coupled to the enclosure. The tubing coupler can be further coupled to the air compressor and configured to cause the pressurized gas to be output from the enclosure. Lastly, the embodiment can include an interactive surface coupled to the enclosure.

4 Claims, 5 Drawing Sheets

COMPRESSOR UNIT FOR NEBULIZER

TECHNICAL FIELD

The present invention is generally related to compressor systems, and more particularly, the invention is related to compressor units used for nebulizer therapy.

BACKGROUND

Medical nebulizers are devices well known in the art that nebulize, atomize or aerosolize a fluid medication for delivery to a patient. Nebulizers are frequently used for the delivery of medication to patients suffering from respiratory problems such as, for example, asthma. In general, a nebulizer operates by passing a compressed gas over or near a fluid reservoir containing liquid medication. Liquid medication is drawn or aerosolized into the compressed gas by operation of the Venturi Effect. Nebulizer systems generally employ an air compressor coupled to a nebulizer mask or mouthpiece by tubing configured to transport a compressed gas generated by a nebulizer air compressor to the nebulizer mask or mouthpiece.

Nebulizers and inhalation therapy or medication via nebulizer are often prescribed by physicians for adults and children suffering from respiratory disorders. A patient receiving such therapy is required to breathe with a nebulizer mask or mouthpiece attached for at least several minutes so that aerosolized fluid medication can be administered within the patient's lungs. Patients may be required to breathe through a nebulizer mask in the range of over ten minutes depending on the required dosage and concentration of medication. Children receiving inhalation therapy or medication via nebulizer typically breathe through a nebulizer mask or mouthpiece for a longer period of time to allow for medication contained in a nebulizer fluid reservoir to be fully administered to the child's lungs.

Regular and emergency nebulizer treatments are frequently prescribed to children with respiratory disorders as an alternative to inhaler treatments or for situations when inhaler treatments are less effective. Often, pediatric patients are prescribed nebulizer treatments in lieu of inhaler treatments because of the difficulty in instructing a child on the proper way to accept medication via an inhaler, as an inhaler requires some bare level of knowledge about how to receive the treatment, which is known in the art. Further, while a child may be required to breathe through a nebulizer mask attached to a nebulizer compressor for a period of time, children (because of short attention spans) often find it difficult, distasteful or boring to complete an entire nebulizer treatment. Parents of pediatric patients similarly often find it difficult to get the child to calmly remain tethered to a nebulizer system by a nebulizer mask and tubing coupled to a nebulizer compressor for a complete administering of prescribed or required levels of medication.

The difficulty of safely getting pediatric patients to comfortably remain tethered to a nebulizer system can result in insufficient medication administering via the nebulizer, which can compromise the effectiveness of such a treatment, as parents may often allow a child to abbreviate a treatment if the child expresses discomfort and a desire to remove cease a nebulizer treatment. Hence, a heretofore unaddressed need exists to increase the comfort-level or placate the short attention span of a child undergoing a nebulizer treatment.

SUMMARY OF THE INVENTION

Disclosed are systems for an interactive nebulizer compressor. In one embodiment, the system comprises an air compressor configured to output a pressurized gas. The system further includes an enclosure surrounding the air compressor that further comprises at least one surface configured to accept and secure toy building blocks. The system also includes a tubing coupler coupled to the enclosure that is configured to accept the pressurized gas and output the pressurized gas into tubing coupled to the tubing coupler.

In another embodiment, an interactive nebulizer compressor includes an air compressor configured to output a pressurized gas and an enclosure surrounding the air compressor. The system further includes a tubing coupler coupled to the enclosure, the tubing coupler further coupled to the air compressor and configured to cause the pressurized gas to be output from the enclosure. Finally, the system includes an interactive surface coupled to the enclosure.

DETAILED DESCRIPTION

The systems and methods described herein relate to medical nebulizer systems, particularly nebulizer compressors that incorporate interactive, educational or entertainment features for patients requiring nebulizer treatments. Exemplary embodiments are discussed with reference to the figures, and although the systems are described in detail, a person of ordinary skill in the art would appreciate that various modifications are feasible within the scope of the present claims and specification.

Figure 1:
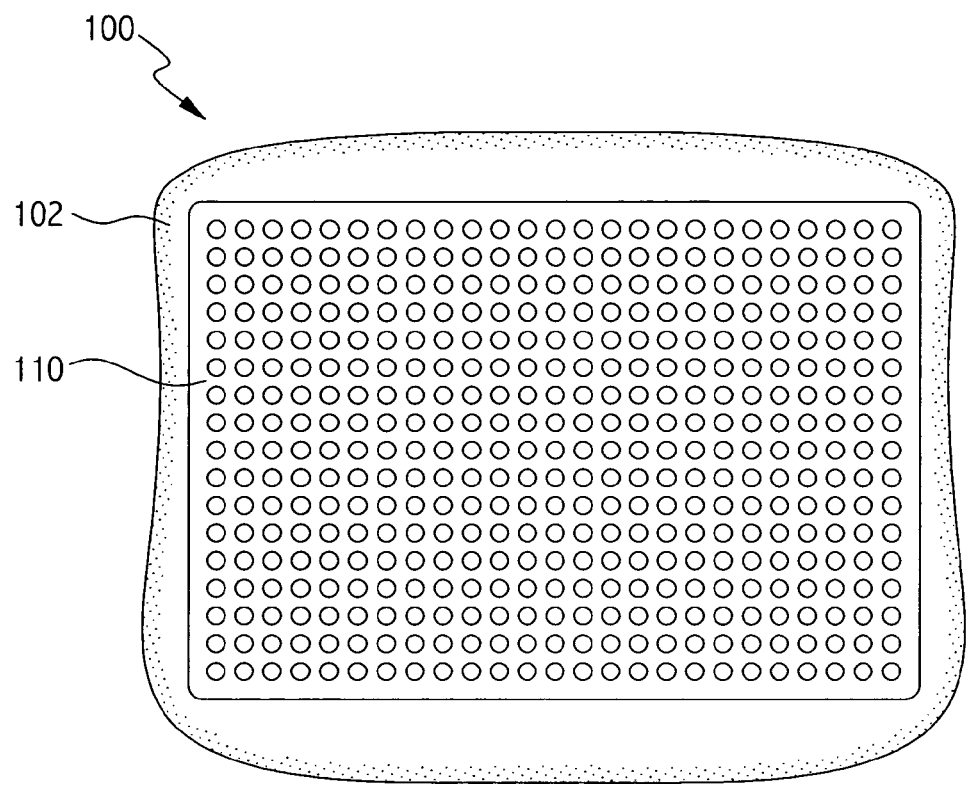
FIG. 1 is a top plan view of an embodiment in accordance with the disclosure.

FIG. 1 depicts a top plan view of an embodiment in accordance with the present disclosure. The interactive nebulizer compressor 100 includes an enclosure 102 and an interactive surface 110 (which interactive surface will be further described below). The interactive nebulizer compressor 100 also includes an air compressor (not shown) within the enclosure 102 that generates a compressed gas that is utilized for delivery and aerosolizing of a medication via a nebulizer mask or mouthpiece. A nebulizer mask or mouthpiece is a component of a medical nebulizer system that is known in the art and can take varying forms to facilitate pediatric nebulizer therapy via the mouth and/or nose of a patient.

Figure 2:
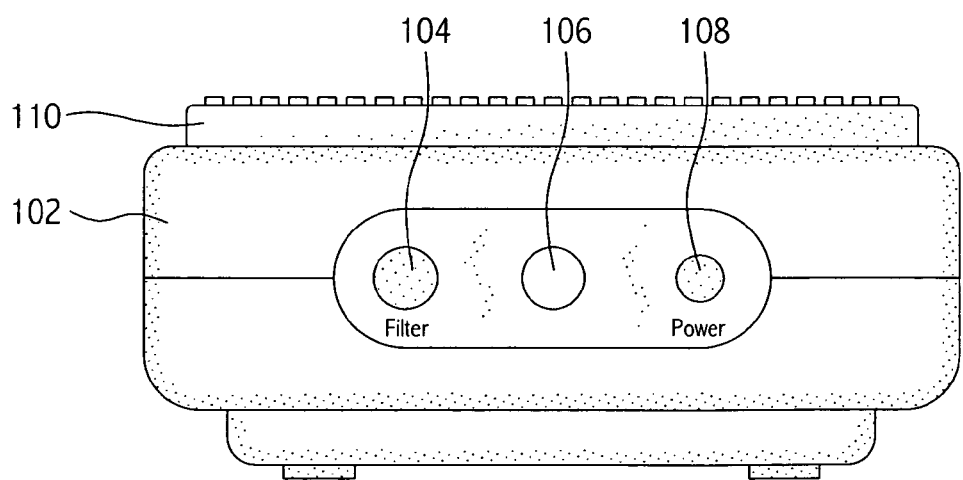
FIG. 2 is a front plan view of the embodiment of FIG. 1.

FIG. 2 depicts a front plan view of the interactive nebulizer compressor 100 and other additional features of the embodiment. The interactive nebulizer compressor 100 can also include a filter 104 that filters air incoming to the air compressor before a compressed gas is produced and utilized for nebulizer therapy. The interactive nebulizer system can be activated via a power switch 108 to enable the air compressor to output a compressed gas for medication delivery.

The enclosure 102 of the interactive nebulizer compressor 100 also includes a tubing coupler 106, which couples the air compressor within the enclosure to tubing that in turn can be coupled to a nebulizer mask or mouthpiece. As noted above, the interactive nebulizer compressor 100 includes an enclosure 102 with an interactive surface 110 that can be utilized to entertain, educate, or otherwise occupy the time of a pediatric patient receiving nebulizer therapy. The interactive surface 110 increases the chances that a pediatric patient will not express discomfort, impatience or boredom during nebulizer therapy, which as noted above can often span a significant period of time. Therefore, the interactive nebulizer compressor 100 further increases the chances that a successful and complete administering of prescribed or required medication will occur during pediatric nebulizer therapy.

The interactive surface 110 depicted in FIGS. 1 and 2 is configured to accept and secure toy blocks having a structure similar to, or compatible with, toy blocks marketed under the trade name LEGO®. The interactive surface 110 can also be configured to accept LEGO® toy blocks or toy blocks marketed under other names and sold by other manufacturers with differing specifications. As depicted, the interactive surface 110 includes a plurality of circular pegs that can be sized according to the specifications of these various toy blocks sold in the market. More specifically, it would be appreciated that various toy blocks are sold in the market with apertures configured to accept a peg either from another toy block or a surface such as the interactive surface 110.

The size of the plurality of pegs can be varied according to the size of apertures within various toy blocks in order to accept and secure toy blocks to the surface. It would also be appreciated that the shape or layout on the interactive surface 110 of the plurality of pegs can also be varied in order to accept various toy blocks on the market. While toy blocks such as those marketed under the trade name LEGO® can be used in conjunction with the interactive surface 110, it would be appreciated that many types of building blocks, erector sets, or other interactive building sets can be used in accordance with the disclosure.

A person of ordinary skill in the art would appreciate that the interactive surface 110 can be configured to accept various forms of interactive and educational activities for a pediatric patient receiving nebulizer therapy in accordance with the invention. As non-limiting examples, an interactive surface can be configured with a puzzle or puzzle-like games or activity sets offering visual and tactile feedback similar to those that are commonly available for infants.

Figure 3:
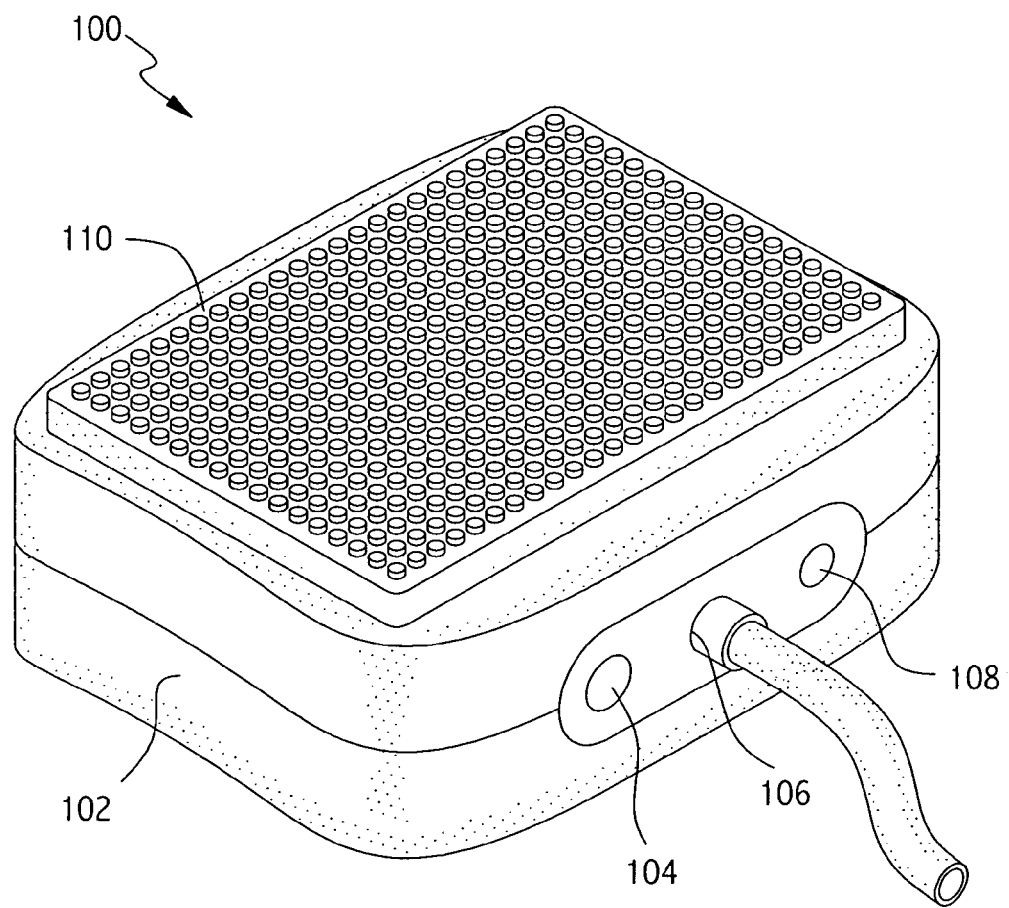
FIG. 3 is a perspective view of the embodiment of FIG. 1.

FIG. 3 depicts a perspective view of the embodiment of FIGS. 1 and 2. FIG. 3 also depicts tubing coupled to the tubing coupler 106 of the interactive nebulizer compressor 100. As noted above, tubing is used to couple the air compressor within an interactive nebulizer compressor 100 to a nebulizer mask or mouthpiece. The air compressor delivers a compressed gas via the tubing coupler 106 and tubing to a nebulizer mask or mouthpiece so that aerosolized or atomized medication can be inhaled and delivered to the lungs of a patient. The tubing carries a compressed gas to a nebulizer fluid or medication reservoir, where it creates an aerosolized form of proper medication that can be inhaled by a patient. The process of aerosolizing medication in a fluid reservoir and the incorporation of a nebulizer mouthpiece or mask with a length of tubing to a nebulizer compressor are known to and appreciated by a person of ordinary skill in the art.

Figure 4:
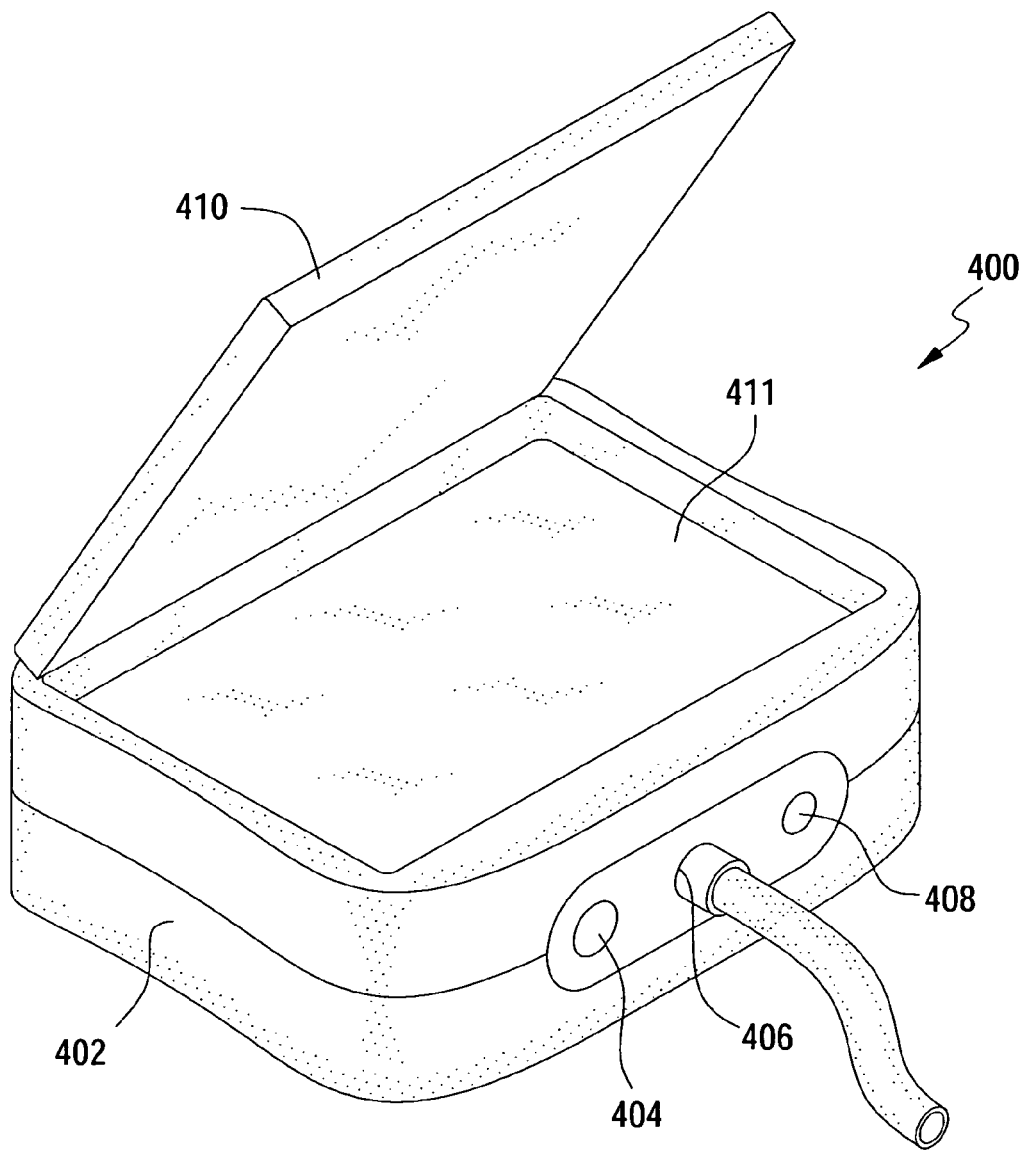
FIG. 4 is a perspective view of an alternative embodiment in accordance with the disclosure.

FIG. 4 depicts a perspective view of an alternative embodiment of an interactive nebulizer compressor 400. The embodiment includes an interactive surface 410 similar to that of the embodiment depicted in FIGS. 1-3; however, the interactive surface 410 is also movable to reveal a storage area 411 located beneath the interactive surface 410. The storage area 411 can be used to store toy blocks or other articles used in conjunction with the interactive surface 410 or other items unrelated to the interactive surface 410. The storage area 411 can also be used to store tubing and/or a nebulizer mask or mouthpiece used for the delivery of medication. The interactive nebulizer compressor 400 also includes a enclosure 402 housing an air compressor (not shown), which compresses air drawn through air filter 404 and delivers a compressed gas via tubing coupler 406 for the purposes of nebulizer therapy.

Figure 5:
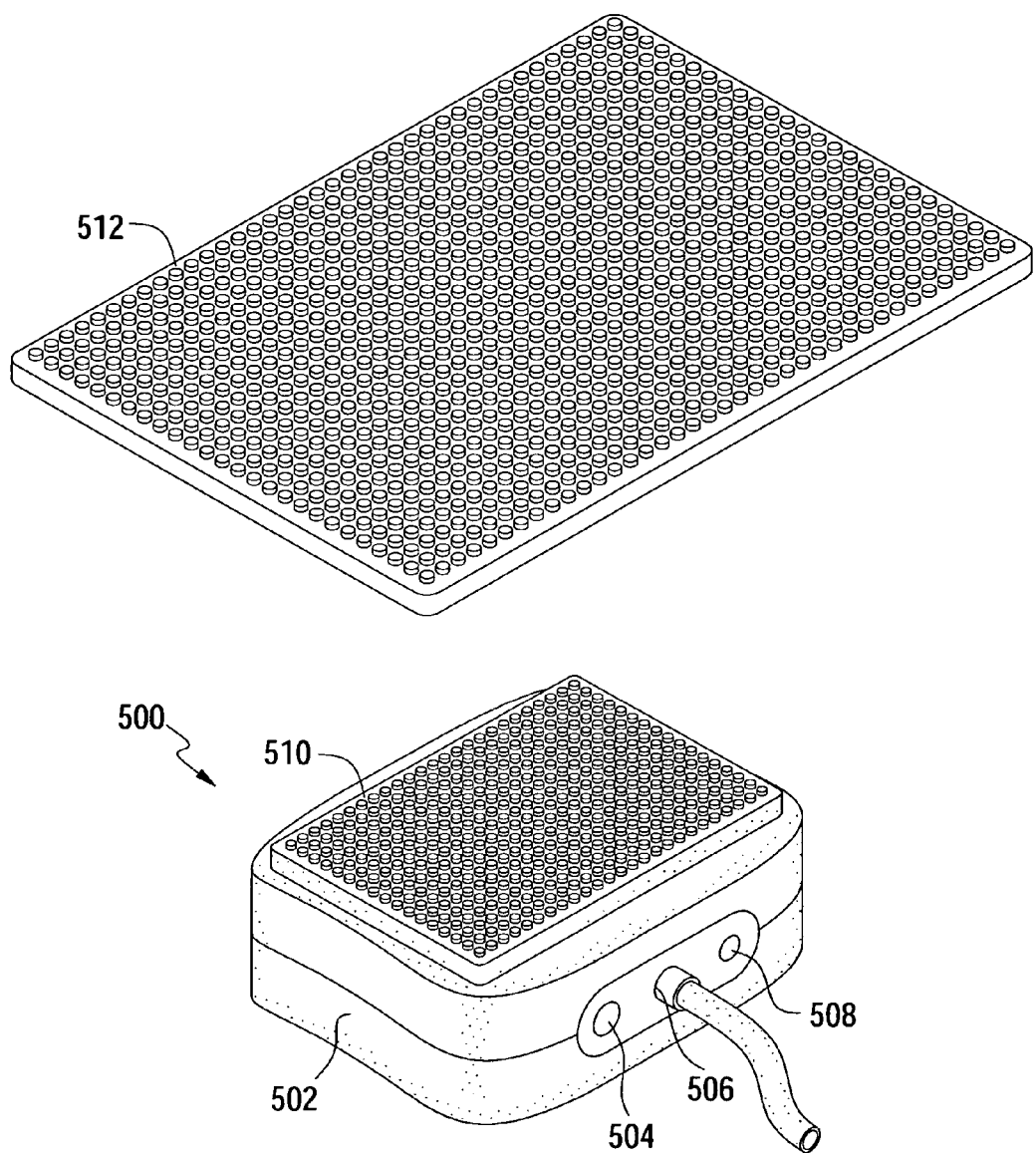
FIG. 5 is a perspective view of an alternative embodiment in accordance with the disclosure.

FIG. 5 depicts an alternative embodiment of an interactive nebulizer compressor 500. The embodiment includes similar components of previously disclosed embodiments according to the disclosure. However, in addition, the embodiment includes a supplemental interactive surface 512 that can be coupled to the interactive surface 510 to create a larger interactive area that is coupled to the enclosure 502 of the interactive nebulizer compressor 500. The supplemental interactive surface 512 can be configured to be removable from the interactive surface 510 and can also be configured to secure to the interactive surface 510 by including on its underside apertures similarly shaped and sized with a plurality of pegs of the interactive surface 510 so that the pegs of interactive surface 510 secure to apertures of supplemental interactive surface 512. A person of ordinary skill in the art would appreciate that this would entail the supplemental interactive surface 512 securing to interactive surface 510 in a manner similar to that of toy blocks marketed under the trade name LEGO® and other similar or equivalent building blocks, erector sets or other similar products.

Figure 6:
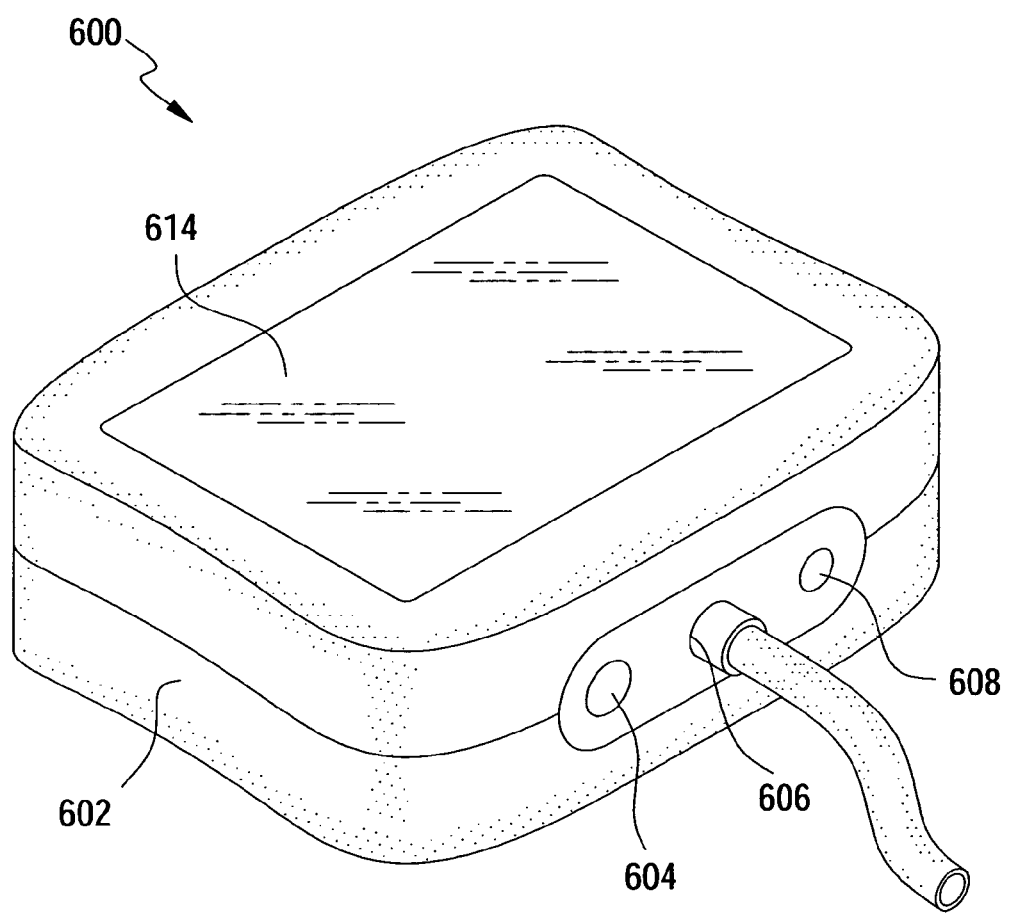
FIG. 6 is a perspective view of an alternative embodiment in accordance with the disclosure.

FIG. 6 illustrates an alternative embodiment in accordance with the disclosure that includes an alternative interactive surface 614. The interactive nebulizer compressor 600 also includes a enclosure 602 housing an air compressor (not shown), which compresses air drawn through air filter 604 and delivers a compressed gas via tubing coupler 606 for the purposes of nebulizer therapy, similar to embodiments disclosed above. In addition, interactive surface 614 is configured with a video display unit that can used for the display of movies or other video as well as for interactive activities that can occupy a pediatric patient receiving nebulizer therapy. In addition, interactive surface 614 can be configured with touch sensitive or touchscreen video display unit that can receive tactile input from a user and be used in conjunction with educational or interactive video presentations or computer systems. As a non-limiting example, a touch sensitive video display unit can be used in conjunction with gaming or educational software to provide an interactive experience for a pediatric patient receiving nebulizer therapy.

It should be emphasized that the above-described embodiments are simply possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and protected by the following claims.

For example, the interactive surface disclosed in the above embodiments may be modular. In other words, although the above described embodiments depict different embodiments with slightly differing examples of an interactive surface, it would be appreciated that the interactive surface may be removable and replaceable with an interactive surface offering a new or different interactive experience. For example, an interactive surface configured to accept and secure a toy building block may be removable and replaceable with an interactive surface configured with a video display unit to offer a pediatric patient a variety of interactive experiences during nebulizer therapy.

Therefore, having thus described the invention, at least the following is claimed:

1. An interactive nebulizer compressor, comprising:
    an air compressor configured to output a pressurized gas,
    an enclosure surrounding the air compressor, the enclosure further comprising at least one surface, the at least one surface having a first surface area, configured to accept and secure toy building blocks, and
    a tubing coupler coupled to the enclosure, the tubing coupler configured to accept the pressurized gas and output the pressurized gas into tubing coupled to the tubing coupler,
    wherein the at least one surface is further configured to accept and secure a supplemental interactive surface, the supplemental interactive surface having a second surface area, configured to accent and secure toy building blocks, the second surface area being larger than the first surface area.

2. The interactive nebulizer compressor of claim 1, wherein the enclosure further comprises at least one surface having a first plurality of pegs coupled to the enclosure, the first plurality of pegs configured to accept and secure at least one toy building block having at least one aperture similarly sized and shaped to at least one of the first plurality of pegs.

3. The interactive nebulizer compressor of claim 1, further comprising:
    a storage area within the enclosure, wherein at least one surface of the enclosure opens to provide access to the storage area.

4. The interactive nebulizer compressor of claim 1, wherein the supplemental interactive surface comprises a second plurality of pegs coupled to the supplemental enclosure, the second plurality of pegs configured to accept and secure at least one toy building block having at least one aperture similarly sized and shaped to at least one of the second plurality of pegs.

* * * * *